(12) United States Patent
Perloff

(10) Patent No.: US 7,968,314 B2
(45) Date of Patent: Jun. 28, 2011

(54) METHODS EMPLOYING A MULTI-TIME POINT IC50 ASSAY FOR SELECTING TIME POINTS FOR TIME DEPENDENT INHIBITION ASSAYS OF A TEST COMPOUND

(75) Inventor: Elke S. Perloff, Somerville, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 346 days.

(21) Appl. No.: 12/243,447

(22) Filed: Oct. 1, 2008

(65) Prior Publication Data

US 2009/0087872 A1    Apr. 2, 2009

Related U.S. Application Data

(60) Provisional application No. 60/976,653, filed on Oct. 1, 2007.

(51) Int. Cl.
*C12Q 15/09*    (2006.01)
(52) U.S. Cl. .......................................... 435/69.2; 435/25
(58) Field of Classification Search ................. 435/69.2, 435/25
See application file for complete search history.

(56) References Cited

U.S. PATENT DOCUMENTS 7,608,616 B1 *  10/2009  Cartt ............................. 514/221

OTHER PUBLICATIONS

Perloff E. et al. Validation of Cytochrome P450 Time Dependent Inhibition Assays. Xenobiotica 2009 39(2)99-112.*
Ghanbari, F., Rowland-Yeo, K., Bloomer, J.C., Clarke S.E., Lennard, M.S., Tucker, G.T., and Rostami-Hodjegan, A., "A Critical Evaluation of the Experimental Design of Studies of Mechanism Based Enzyme Inhibition, With Implications for In Vitro-In Vivo Extrapolation," Curr. Drug Metab., Apr. 2006; 7(3):315-34.
Obach, R. S., Walsky, R. L., and Venkatakrishnan, K., "Mechanism-Based Inactivation of Human Cytochrome P450 Enzymes and the Prediction of Drug-Drug Interactions," Drug Metab. Dispos., Feb. 2007; 35(2):246-55, Epub Nov. 8, 2006.

* cited by examiner

*Primary Examiner* — Ralph Gitomer
(74) *Attorney, Agent, or Firm* — Hoffmann & Baron, LLP

(57) ABSTRACT

The invention provides a method of evaluating metabolism-based drug interactions. The method involves selecting time points for the determination of the inactivation rate constant of a time-dependent enzyme inhibitor based on the results of a multi-time point IC50 test. Advantageously, with the subject invention, the determination and use of the multi-time point IC50 test provides an indication of the inactivation rate of a test compound and eliminates trial and error tests associated with the selection of appropriate assay conditions for the second assay conducted to determine the inactivation rate constant of the test compound.

9 Claims, 4 Drawing Sheets

METHODS EMPLOYING A MULTI-TIME POINT IC50 ASSAY FOR SELECTING TIME POINTS FOR TIME DEPENDENT INHIBITION ASSAYS OF A TEST COMPOUND

CROSS-REFERENCE TO RELATED APPLICATION

This application claims priority to U.S. Provisional Patent Application No. 60/976,653, filed Oct. 1, 2007, the entire contents of which are hereby incorporated by reference.

FIELD OF THE INVENTION

The subject invention is directed to methods of evaluating metabolism-based drug interactions, more particularly, of evaluating the ability of a test compound to inhibit catalytic activity of a target enzyme.

BACKGROUND OF THE INVENTION

Inhibition of enzymes is a major mechanism of metabolism-based drug interactions. This enzyme inhibition is typically evaluated using in vitro models during drug discovery and development, the results of which are generally submitted in regulatory submissions. One such type of enzyme inhibition is time- and cofactor (e.g., NADPH (nicotineamide adenine dinucleotide phosphate))-dependent inhibition (TDI). In this type of inhibition, the inhibitor is generated from the test compound (which may or may not be a direct inhibitor itself) during the assay by an enzyme present in the reaction mix.

Currently, the typical in vitro test for TDI is cumbersome and requires a great deal of trial and error in testing. The general test includes two separate and sequential assays: first, the IC50 shift experiment; and second, a kinetic experiment (referred to as the $K_I/K_{inact}$ determination). The IC50 shift experiment typically includes an assay of various concentrations of the test compound in either the presence or absence of certain cofactors (e.g., NADPH or a NADPH regenerating system), with subcellular fractions containing the target enzyme of interest. At one predetermined time, typically about 30 minutes, a fraction of this initial incubation is diluted (typically at ratios of 1:5 to 1:20) into a secondary incubation, which contains a probe substrate (at a concentration of approximately the $K_m$ of the reaction) along with the enzyme of interest and cofactors. After a second incubation time for the diluted concentration, which is dictated by the probe substrate, the reaction is stopped and the amount of metabolite formed at each condition (each concentration, with and without the cofactor) is measured and expressed as a percent of control (control being 0% concentration of the test compound). The IC50 value, that is, the test compound concentration associated with 50% decrease in metabolite formation, may be calculated for both cofactor conditions, i.e. in the presence of the cofactor and in the absence of the cofactor. A significant difference in the IC50 values between the two cofactor conditions (IC50 value without cofactor being greater than the IC50 value with cofactor, known as an "IC50 shift") generally indicates TDI by the test compound, and a second, follow-up experiment is conducted to determine the TDI values.

The second experiment is the $K_I/K_{inact}$ determination, which measures the kinetic parameters for TDI. This assay uses the same general design as the IC50 test, assaying multiple concentrations of the test compound and an enzyme of interest in the presence of certain cofactors. In this experiment, however, at several predetermined time points, a fraction of the primary incubation is diluted into a secondary incubation, which contains a high concentration (at a concentration above the $K_m$ of the reaction, preferably 5-10× the $K_m$) of the probe substrate, and the cofactors. After a second incubation time for the diluted concentration, the reaction is stopped and the amount of metabolite formed at each concentration is determined. For each test compound concentration, the degree of metabolism (expressed as the natural log of percent of control) is plotted against the pre-incubation time. The slope associated with each test compound concentration is determined and plotted against the test compound concentration. This data set is then used to derive kinetic parameters for TDI ($K_I$ and $K_{inact}$) using non-linear regression or other techniques.

A problem with the above test procedure is in determining the appropriate time points at which to dilute the incubation in the $K_I/K_{inact}$ assay. For example, if the test compound acts rapidly (i.e., metabolizes quickly), the dilutions should preferably take place at quicker intervals in order to achieve better slope determinations and thus, more accurate results. By contrast, if the test compound acts slower, the dilutions should desirably take place at longer intervals to permit sufficient time to achieve accurate results. The problem lies in knowing whether the test compound will act rapidly or slowly, which is not known from a typical IC50 shift experiment. Without knowing whether the test compound is rapid or slow, the kinetic experiments may require iterative trial and error in testing various sets of incubation times to get accurate results. Such trial and error is cumbersome and adds substantial cost to the procedure.

SUMMARY OF THE INVENTION

In one embodiment of the present invention, there is provided a method of evaluating the ability of a test compound to inhibit catalytic activity of a target enzyme, the method including the steps of performing a first assay of the test compound. The first assay includes the steps of: preparing a first set of samples of the test compound and the target enzyme, the first set including samples containing the target enzyme and varying concentrations of the test compound; preparing a second set of samples of the test compound and the target enzyme, the second set including samples containing the target enzyme and varying concentrations of the test compound; evaluating the amount of metabolite formed in the first set of samples after diluting the samples at a first time interval to obtain first results; and evaluating the amount of metabolite formed in the second set of samples after diluting the samples at a second time interval to obtain second results, the second time interval being different from the first time interval. The method further includes the steps of: comparing the first and second results, selecting time points for a secondary inhibition assay of the test compound based on the comparison, and performing a secondary inhibition assay. The secondary inhibition assay includes the steps of: preparing a secondary set of samples of the test compound and the target enzyme, the secondary set including samples containing the target enzyme and varying concentrations of the test compound; and evaluating the amount of metabolite formed in the secondary set of samples after diluting the samples at the selected time points. Advantageously with the subject invention, the determination and use of the selected time points provides an indication of the metabolizing rate of the test compound and an elimination of trial and error tests in the second assay to compare results based on the actual metabolization rate.

These and other features of the invention will be better understood through a study of the following detailed description and accompanying drawings.

DETAILED DESCRIPTION OF THE INVENTION

The invention provides a method of evaluating metabolism-based drug interactions. It particularly provides a method of evaluating metabolism-based drug interactions by incorporating a multi-time period IC50 test procedure. As used herein, the IC50 test is referred to as the test to determine the concentration of a test compound wherein there is associated a 50% decrease in metabolite formation.

As used herein, "NADPH" refers to nicotinamide adenine dinucleotide phosphate. Also as used herein, "+NADPH" refers to conditions where NADPH is present, while "−NADPH" refers to conditions where NADPH is not present.

Figure 1:
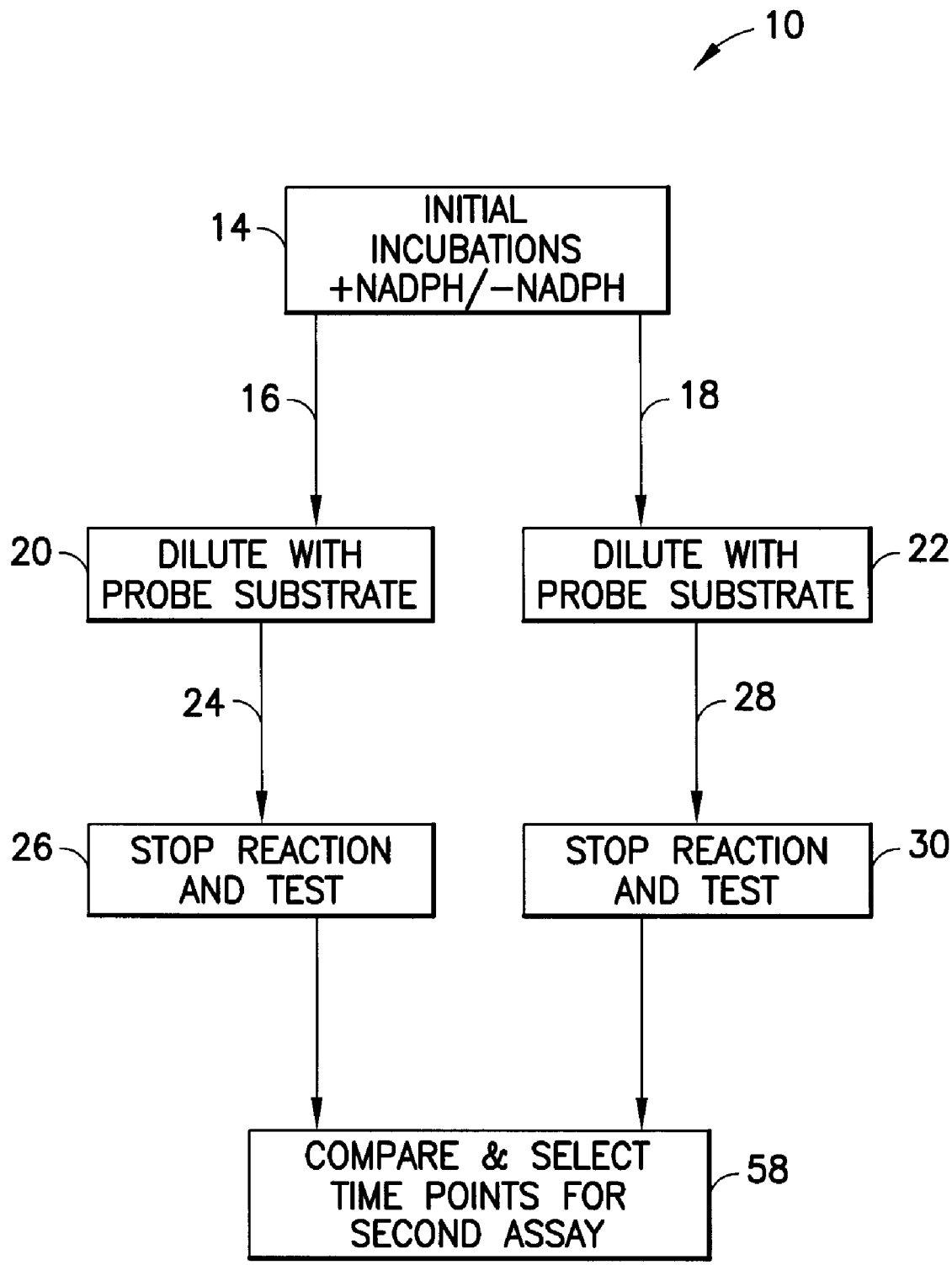
FIG. 1 is a schematic representation of the first assay of the present invention.
Figure 2:
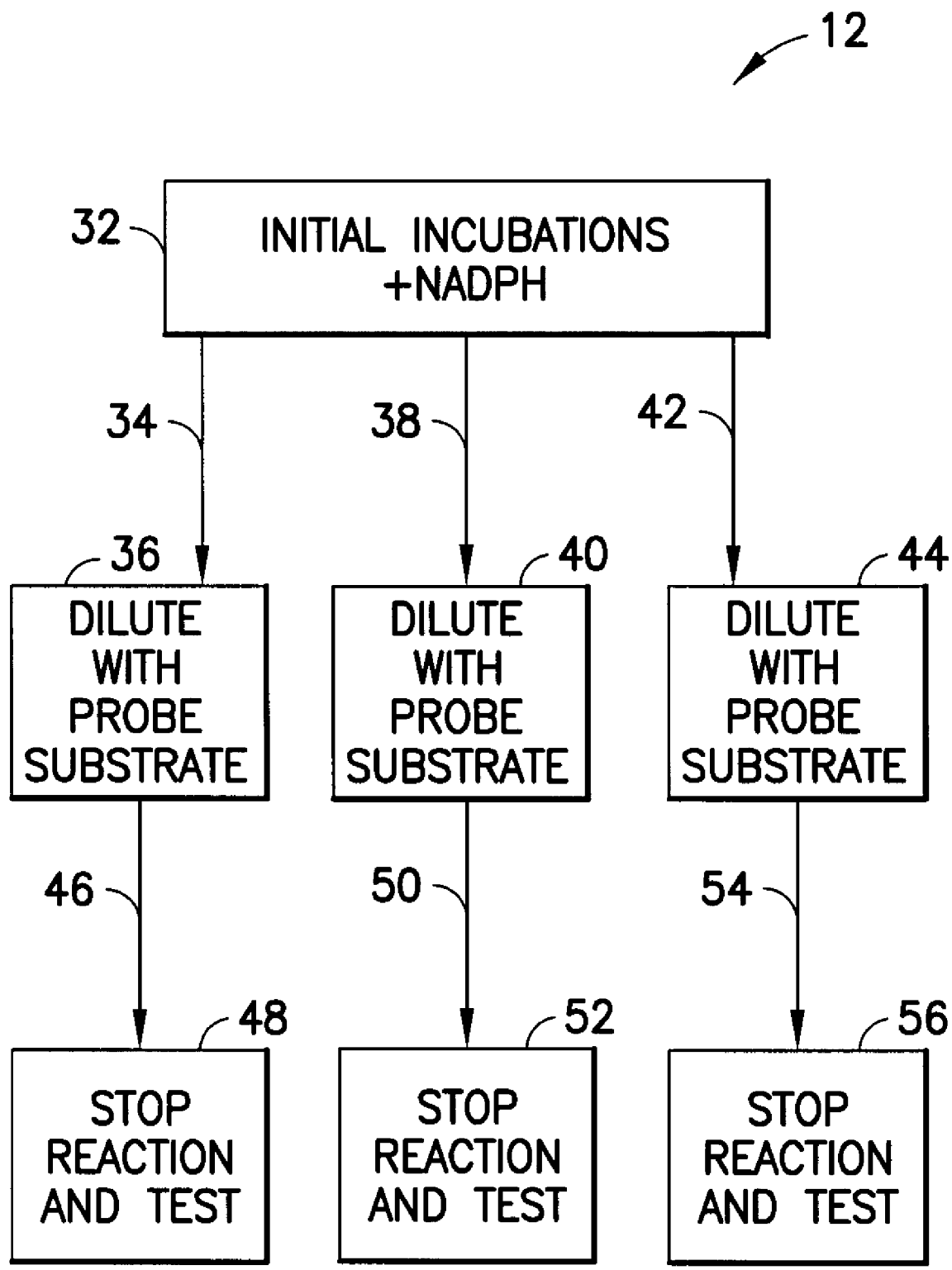
FIG. 2 is a schematic representation of the second assay of the present invention.

With reference to FIGS. 1 and 2, there is depicted an embodiment of the present invention, which includes two separate assays, a first assay 10 and a second assay 12, which are described more fully below.

The First Assay

With reference to FIG. 1, the first assay 10 is useable to determine the presence of an IC50 shift of a test compound relative to a target enzyme. The first assay 10 includes a first step 14, which includes preparing samples containing various concentrations of a test compound in the presence of a target enzyme. A set of samples are prepared, some of which include cofactors, while others do not include cofactors. Any desired cofactors suitable for the target enzyme may be used. Preferably, for studying a target enzyme of cytochrome P450, the cofactors include NADPH and/or NADPH-regenerating systems. The concentrations of the test compound may be in any amount desired, and may include any concentration from 0% to 100% (including a control concentration of 0%).

The first step 14 also includes an initial incubation conducted preferably at approximately 37° C., but may be conducted at higher or lower temperatures, depending upon the target enzymes being evaluated.

The target enzyme may be contained in subcellular fractions in the test samples. Preferably, the enzyme used is cytochrome P450. However, any acceptable enzyme may be used in the assay to evaluate the inhibition of catalytic activity thereof. Alternative target enzymes may include UDP-glucuronosyltransferases, A-acetyltransferases, flavine monooxygenases, or other enzymes that might be susceptible to TDI.

The initial preparations are allowed to incubate for at least two predetermined periods of time. After each time interval, a fraction of the primary incubation is diluted into a secondary incubation. This secondary incubation includes a probe substrate, and additionally includes the selected cofactor. In the embodiment shown in FIG. 1, first and second time periods 16 and 18 are selected. After each time period 16, 18, the initial concentration is diluted with the secondary incubation. Preferably, a step 20 of diluting a first fraction of the primary incubation occurs after the first time period 16. The first time period 16 may be between about 5 minutes to about 15 minutes, more preferably about 10 minutes. Preferably, a step 22 of diluting a second fraction of the primary incubation occurs after the second time period 18. The second time period 18 may be between about 25 minutes and about 35 minutes, more preferably about 30 minutes. The second time period 18 is to be different from, preferably greater than, the first time period 16. In one preferred embodiment, a first fraction of the primary incubation is diluted at about 10 minutes, and a second fraction of the primary incubation is diluted at about 30 minutes. Additional fractions of the primary incubation may be diluted at different times to provide additional data points.

Any level of dilution of the initial incubation may be used. Preferably, the amount of dilution is in a ratio of from about 1 to 5 to about 1 to 20. It is preferred that the concentration of the probe substrate be equal to approximately the $K_m$ of the reaction.

Any probe substrate may be used in the step 20 of the first dilution and the step 22 of the second dilution. Generally, the particular probe substrate selected will depend upon the target enzyme selected. Possible examples for probe substrates include midazolam (CYP3A4), phenacetin (CYP1A2), diclofenac (CYP2C9), dextromethorphan (CYP2D6), S-mephenytoin (CYP2CP), bupropion (CYP2B6), amodiaquine (CYP2C8), and testosterone (CYP3A4).

After diluting with the respective probe substrates, the first and second dilutions are each incubated. The post-dilution incubation period is determined by the respective probe substrate.

After a first incubation time 24, which is preferably a time sufficient for the metabolism of the probe substrate after the first dilution 20, a step 26 occurs of stopping the reaction for the first dilution. The amount of probe substrate metabolite formed at each particular condition (e.g., the various concentrations and presence or absence of cofactors) for the first dilution may then be measured.

After a second incubation time 28, a step 30 of stopping the reaction for the second dilution occurs. As with the first dilution, the amount of probe substrate metabolite formed at each particular condition for the second dilution may then be measured. The post-dilution incubation times 24 and 28 may be any time desired, depending upon the probe substrate used. Preferably, the post-dilution incubation times 24 and 28 are between about 5 to about 20 minutes. In a preferred embodiment, and to achieve best comparative results, the incubation times after the first dilution 24 and the incubation time after the second dilution 28 are the same (within reasonable error), but may vary if desired (understanding that the starting times for each may vary). By having the same post-dilution incubation times, the achieved test results are in best condition for comparative analysis.

After the reactions are stopped, the various levels of probe substrate metabolite in the samples are determined by testing (steps 26 and 30, respectively). Any known means to measure the amount of probe substrate metabolite that has been formed may be used. In a preferred embodiment, the method of measuring the amount of probe substrate metabolite formed is via mass spectrometry.

In one embodiment, the amount of metabolite formed at each condition (which includes all levels of test compound concentration as well as the presence or absence of NADPH) is considered as a percentage of the control. The "control" measurement is determined as the amount of metabolite formed with a test compound concentration of 0% in the presence of the target enzyme and the probe substrate for the respective condition (with or without cofactors). As explained above, the percentages of control may then be used to calculate the IC50 values for both the +NADPH concentrations and the −NADPH concentrations. As explained above, a significant difference in the IC50 values between the +NADPH and the −NADPH groups generally indicates TDI. With an indication of TDI, the second assay 12 may be conducted to better evaluate the test compound's ability to inhibit catalytic activity of the target enzyme.

The Second Assay

The second assay 12 may include an experiment to determine the kinetic parameters for the test compound relative to the target enzyme. With reference to FIG. 2, the second assay 12 may incorporate the same general assay design as the first assay 10, including an initial step 32 of preparing a new set of samples (not utilized in the first assay 10) of multiple concentrations of the test compound and target enzyme. The target enzyme may be contained in subcellular fractions in the initial preparations. Preferably, the second assay 12 is conducted in the presence of the desired cofactors, most particularly the cofactors used in the first assay 10. The second assay 12 may be conducted at any temperature suitable for the incubation of the samples, and preferably is conducted at about 37° C. In the second assay 12, a fraction of the primary incubation is diluted into a secondary incubation at predetermined multiple time points as discussed in more detail below. As with the first assay 10, the secondary incubation in the second assay 12 contains the cofactors of interest. Unlike with the first assay 10, the secondary incubation in the second assay 12 preferably contains a high concentration (preferably, 5-10× of the $K_m$ of the reaction) of the probe substrate.

FIG. 2 depicts one embodiment of the invention incorporating a multiple time point second assay 12. By way of non-limiting example, after a first time point 34, step 36 of diluting a first fraction of the primary incubation into a secondary incubation occurs. After a second time point 38, step 40 of diluting a second fraction of the primary incubation into a secondary incubation occurs. Finally, after a third time point 42, step 44 of diluting a third fraction of the primary incubation into a secondary incubation occurs. It is preferred that the first, second, and third time points 34, 38 and 42 be different. More or less time points may be utilized. Each of the secondary incubations includes the probe substrate and cofactor of interest.

After dilution of the fractions of the primary incubation, the diluted compositions are allowed to incubate for a time sufficient for the probe substrate to be metabolized. Referring to FIG. 2, after a first post-dilution incubation time 46, step 48 of stopping the first dilution occurs. After a second post-dilution incubation time 50, step 52 of stopping the second dilution occurs. After a third post-dilution incubation time 54, step 56 of stopping the third dilution occurs. Preferably, the post-dilution incubation times 46, 50 and 54 are the same (within reasonable error), but may vary if desired (even if initiated at different times). By having the same post-dilution incubation times, the achieved test results are in best condition for comparative analysis. The amount of probe substrate metabolite formed at each concentration level and after each dilution time may then be measured (steps 48, 52, 56, respectively).

The data obtained in the second assay 12 may be used to derive kinetic parameters for time- and NADPH-dependent inhibition. As explained above, the degree of metabolism, which may be plotted as the natural log of percent of control, may be plotted against the pre-incubation time. The slope associated with each test compound concentration may be used to derive kinetic parameters for TDI. Preferably, the derivation is achieved using non-linear regression or other known techniques.

Any number of time points may be used in the second assay 12 (i.e., time points where a fraction of the primary incubation is diluted). In a preferred embodiment, there are about 3 to about 10 predetermined time points at which the primary incubation may be diluted into the secondary incubation. The particular time points at which the various dilutions will take place are preferably determined by comparing the results obtained in the first assay 10, as will be explained in more detail below.

Determining Time Points for the Second Assay

With reference to FIG. 1, once the values for the amount of metabolite formed at each condition are obtained in the first assay 10, one may then undertake the step 58 of comparing and evaluating the results. In one embodiment, the amount of metabolite formed in the concentrations that have been diluted after the first time period is compared to the amount of metabolite formed in the concentrations that have been diluted after the second time period. Preferably, the comparison of the two results is achieved by using graphic depictions of the results. In one embodiment, a linear plot for each condition is graphed and evaluated. Most preferably, the results obtained from the dilutions prepared at the first time period are graphed separately from the results obtained from the dilutions prepared at the second time period. As will be readily recognized by one skilled in the art, similar methodology is applied to any additional time points.

A significant difference in the over-time formation of metabolite between the first time period dilution and the second time period dilution (e.g., as determined by comparing the graphs of the two results from the first assay 10) will generally indicate that the test compound is a "slow acting" inhibitor relative to the target enzyme. An insignificant difference in the over-time formation of metabolite between the first time period dilution and the second time period dilution will generally indicate that the test compound is a "rapid acting" inhibitor relative to the target enzyme. Generally, a "rapid acting" inhibitor is one that is substantially metabolized in about 10 minutes or less, while a "slow acting" inhibitor is one that is substantially metabolized in more than about 10 minutes.

Once it has been determined whether the test compound is a slow acting or rapid acting inhibitor, the time points for the second assay may be selected. Preferably, where the test compound is a "rapid acting" inhibitor, the time periods for the second assay may be closer together. Additionally, for a "rapid acting" inhibitor, the first time period is preferably at a time soon after the initial incubation has begun. In one exemplary embodiment, the first time period at which a dilution may take place for a "rapid acting" inhibitor is between approximately 0.5-2 minutes, with subsequent dilutions of the initial incubation taking place between approximately every 0.5-3 minutes thereafter.

Preferably, where the test compound is a "slow acting" inhibitor, the time periods for the second assay may be spaced further apart. Additionally, for a "slow acting" inhibitor, the first time period may begin at a time later after the initial incubation has begun. In one exemplary embodiment, the first time period at which a dilution may take place for a "slow acting" inhibitor is between approximately 5-10 minutes, with subsequent dilutions of the initial incubation taking place between approximately every 5-10 minutes thereafter.

EXAMPLES

Example 1

A two time point IC50 shift experiment was performed for the test compound azamulin, which is known to be a rapid acting inhibitor. The target enzyme used was cytochrome P450 3A4, with midazolam as the probe substrate. Various concentrations of the test agent azamulin were prepared and allowed to incubate. Additionally, some of the initial incubations included NADPH (+NADPH), while others were void of NADPH (−NADPH). One group of concentrations was allowed to incubate for approximately 10 minutes, at which point the initial incubations were diluted and allowed to incubate for 5 minutes. The extent of midazolam metabolite formation was then tested as a percent of control. A second group of concentrations was allowed to incubate for approximately 30 minutes, at which point the initial incubations were diluted and allowed to incubate for 5 minutes. The extent of midazolam metabolite formation in the second group was then tested as a percent of control.

The results are set forth below in Table 1:

TABLE 1

| | IC50 Values (μM) | | |
|---|---|---|---|
| Inhibition Time | +NADPH | −NADPH | Fold Difference |
| 10 minutes | 0.0031 | 0.095 | 31 |
| 30 minutes | 0.0027 | 0.117 | 44 |

Figure 3A:
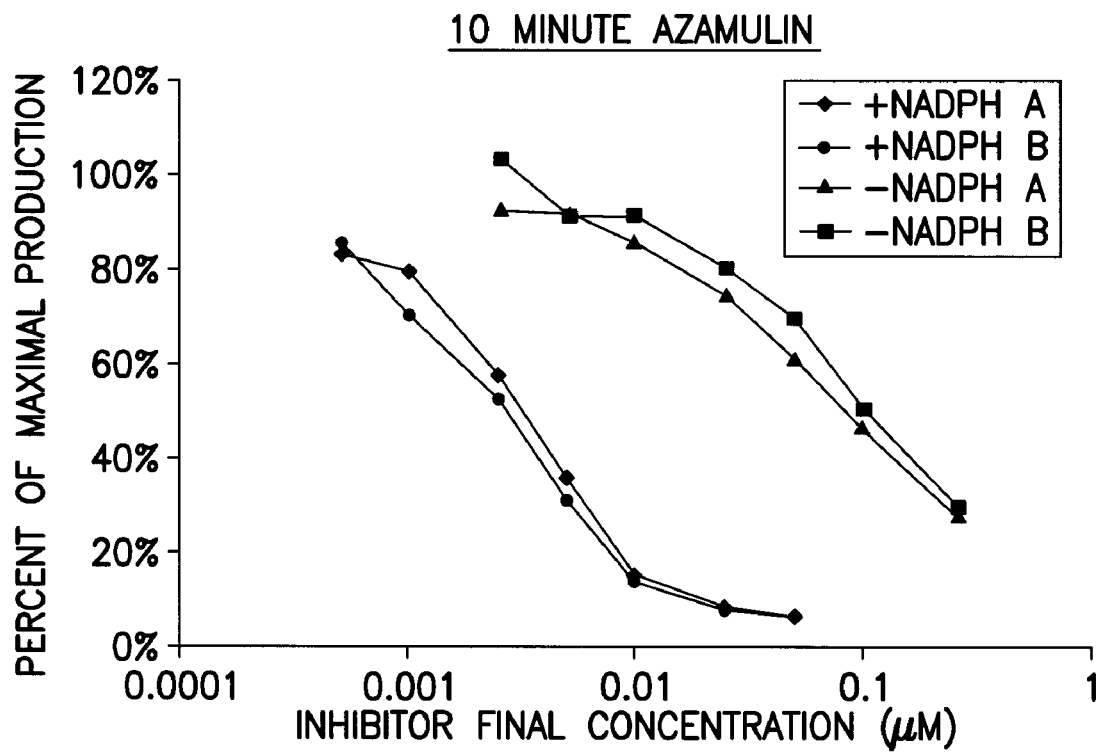
FIGS. 3A and 3B are graphical depictions of the results of a first assay conducted in accordance with the present invention for a rapid acting inhibitor.
Figure 3B:
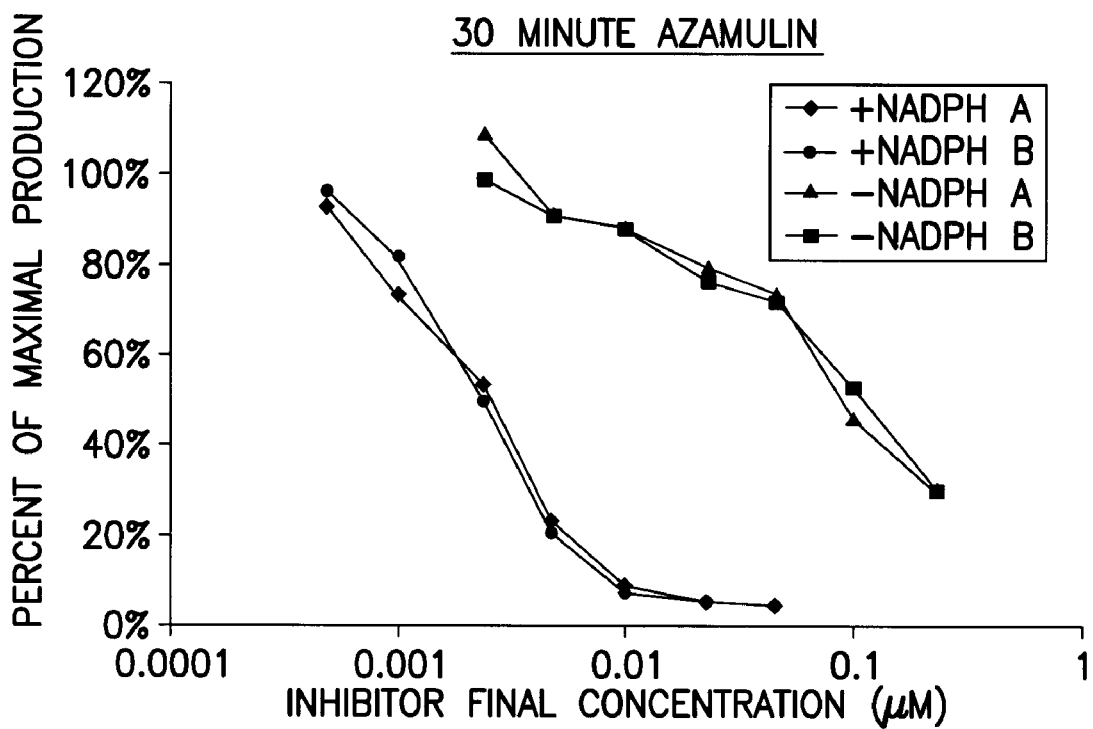

FIGS. 3A and 3B show graphical depictions of the results of this first assay at the various conditions tested. As can be seen in FIGS. 3A and 3B, there is very little difference in the graphical representations of the IC50 values for the dilution after 10 minutes (FIG. 3A) and the dilution after 30 minutes (FIG. 3B). Because there is little difference between the 10-minute dilution and the 30-minute dilution, it is surmised that the test compound has been reacted within about 10 minutes. Thus, azamulin may be considered a "rapid acting" inhibitor and the selected time points for the $K_{inact}$ test should begin sooner, and be spaced closer to each other.

Example 2

A two time point IC50 shift experiment was performed for the test compound verapamil, which is known to be a slow acting inhibitor. The target enzyme used was cytochrome P450 3A4, with midazolam as the probe substrate. Additionally, some of the initial incubations included NADPH (+NADPH), while others were void of NADPH (−NADPH). One group of concentrations was allowed to incubate for approximately 10 minutes, at which point the initial incubations were diluted and allowed to incubate for 5 minutes. The extent of midazolam metabolite formation was then tested as a percent of control. A second group of concentrations was allowed to incubate for approximately 30 minutes, at which point the initial incubations were diluted and allowed to incubate for 5 minutes. The extent of midazolam metabolite formation in the second group was then tested as a percent of control.

The results are set forth below in Table 2:

TABLE 2

| | IC50 Values (μM) | | |
|---|---|---|---|
| Inhibition Time | +NADPH | −NADPH | Fold Difference |
| 10 minutes | 4.7760 | 22.592 | 4.7 |
| 30 minutes | 0.4293 | 26.399 | 61.5 |

Figure 4A:
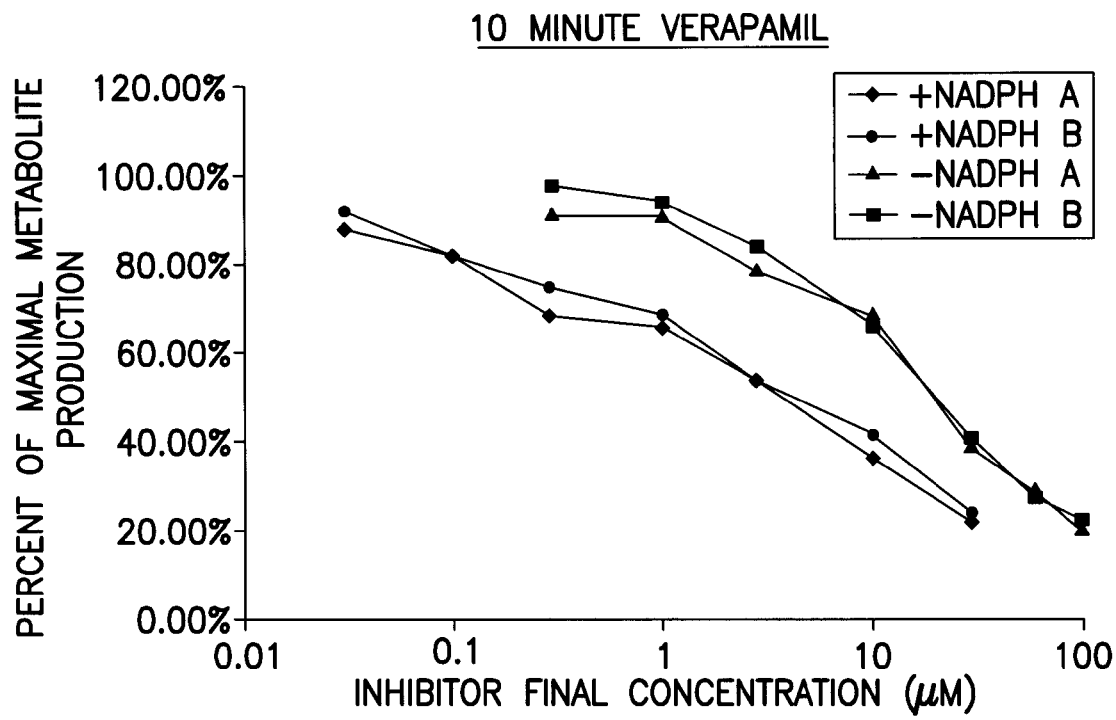
FIGS. 4A and 4B are graphical depictions of the results of a first assay conducted in accordance with the present invention for a slow acting inhibitor.
Figure 4B:
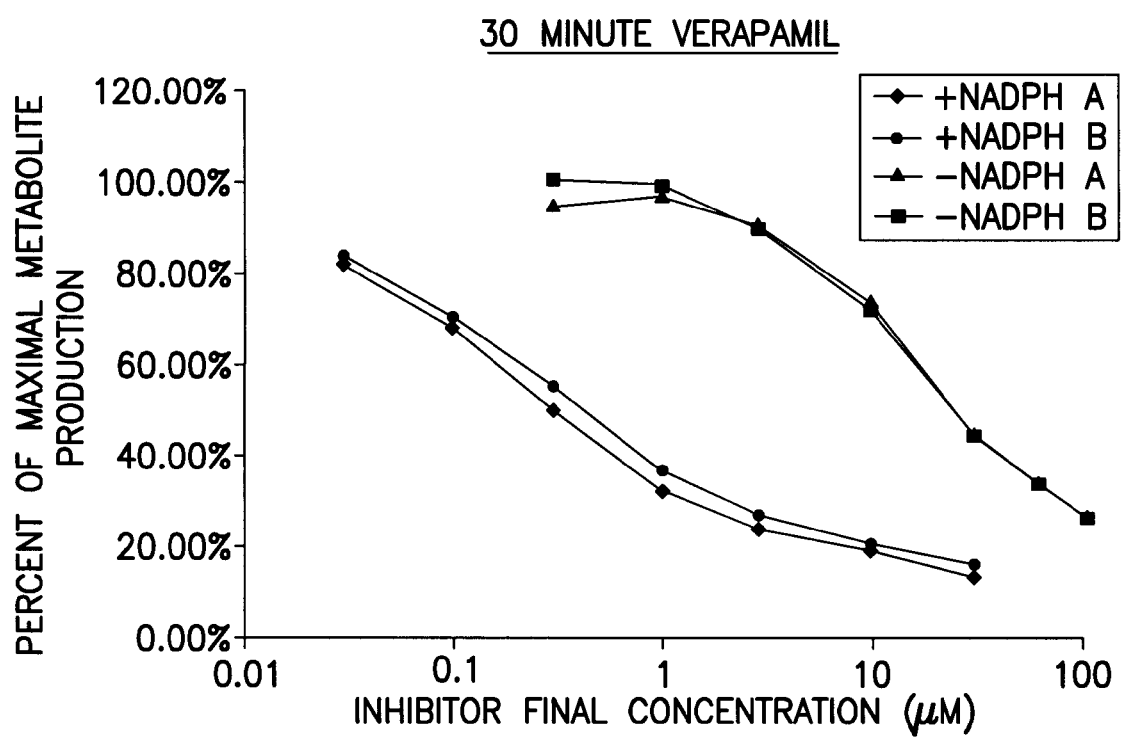

FIGS. 4A and 4B show graphical depictions of the results of this first assay at the various conditions tested. As can be seen in FIGS. 4A and 4B, there is a significant difference in the graphical representations of the IC50 values for the 10 minute dilution (FIG. 4A) and for the dilution after 30 minutes (FIG. 4B). Because there is a significant difference between the 10-minute dilution and the 30-minute dilution, it may be surmised that the test compound has not been significantly reacted until after about 10 minutes. Thus, verapamil may be considered a slow acting inhibitor, and the time points for the $K_{inact}$ test should start later after the initial incubation, and should be more spaced apart to achieve a more accurate test.

What is claimed is:
1. A method of evaluating whether a test compound is a slow or a rapid acting inhibitor of a target enzyme so as to select time points for a time-dependent inhibition assay, comprising the steps of:
   a. performing a first assay of the test compound, said first assay comprising the steps of:
      i. preparing a first set of samples of the test compound and the target enzyme, said first set including samples containing the target enzyme and varying concentrations of the test compound;
      ii. preparing a second set of samples of the test compound and the target enzyme, said second set including samples containing the target enzyme and varying concentrations of the test compound;
      iii. evaluating the amount of products formed from reactants in said first set of samples after diluting the samples at a first time interval to obtain first results; and
      iv. evaluating the amount of products formed from reactants in said second set of samples after diluting the samples at a second time interval to obtain second results, said second time interval being different from said first time interval;
   b. comparing said first and second results to determine whether the test compound is a slow acting inhibitor that substantially inhibits the target enzyme in more than about 10 minutes or a rapid acting inhibitor that inhibits the target enzyme in about 10 minutes or less;
   c. selecting time points for a secondary inhibition assay of the test compound to determine time-dependent kinetics based on whether the test compound is a slow acting inhibitor or a rapid acting inhibitor; and
   d. performing the secondary inhibition assay, said secondary inhibition assay comprising the steps of:
      i. preparing a secondary set of samples of the test compound and the target enzyme, said secondary set including samples containing the target enzyme and varying concentrations of the test compound; and
      ii. evaluating the amount of products formed from reactants in said secondary set of samples after diluting the samples at said selected time points.

2. The method of claim 1, wherein said first, second or secondary set of samples include cofactors comprising NADPH or NADPH regenerating systems.

3. The method of claim 1, wherein the target enzyme comprises cytochrome P450.

4. The method of claim 1, wherein said first time interval is between about 5 minutes and about 15 minutes.

5. The method of claim 1, wherein said second time interval is between about 25 minutes and about 35 minutes.

6. The method of claim 1, wherein said first assay tests the IC50 values of said test compound relative to said target enzyme.

7. The method of claim 1, wherein said second assay tests the kinetic parameters for NADPH-dependent inhibition of said test compound relative to said target enzyme.

8. The method of claim 1, wherein said step of comparing the first and second test results includes creating graphic representations of said first and second results.

9. The method of claim 8, wherein said step of selecting time points includes a comparison of said graphic representations.

* * * * *